United States Patent [19]

Haefliger

[11] Patent Number: 5,077,298

[45] Date of Patent: Dec. 31, 1991

[54] 8α-ACYLAMINOERGOLINES

[75] Inventor: Walter Haefliger, Langnau, Switzerland

[73] Assignee: Sandoz Ltd., Basel, Switzerland

[21] Appl. No.: 547,899

[22] Filed: Jul. 2, 1990

Related U.S. Application Data

[60] Division of Ser. No. 316,363, Feb. 27, 1989, Pat. No. 4,950,672, which is a continuation of Ser. No. 167,826, Mar. 14, 1988, abandoned, which is a continuation of Ser. No. 11,641, Feb. 6, 1987, abandoned, which is a continuation of Ser. No. 690,864, Jan. 11, 1985, abandoned.

[30] Foreign Application Priority Data

Jan. 12, 1984 [DE] Fed. Rep. of Germany ....... 3400853

[51] Int. Cl.$^5$ .................. A61K 31/48; C07D 457/12
[52] U.S. Cl. ........................ 514/288; 546/68
[58] Field of Search .................. 514/288; 546/68

[56] References Cited

U.S. PATENT DOCUMENTS

| | | | |
|---|---|---|---|
| 2,864,822 | 12/1958 | Fornefeld et al. | 546/68 |
| 3,218,323 | 11/1965 | Hofmann et al. | 546/68 |
| 4,348,391 | 9/1982 | Stütz | 546/68 |
| 4,348,392 | 9/1982 | Fehr et al. | 546/68 |
| 4,791,115 | 12/1988 | Haefliger | 546/68 |
| 4,950,672 | 8/1990 | Haefliger | 546/68 |

FOREIGN PATENT DOCUMENTS 622519   4/1981   Switzerland .
628895   3/1982   Switzerland .
2206115 12/1988   United Kingdom .

Primary Examiner—Cecilia Shen
Attorney, Agent, or Firm—Gerald D. Sharkin; Robert S. Honor; Thomas O. McGovern

[57] ABSTRACT

Compounds of formula I

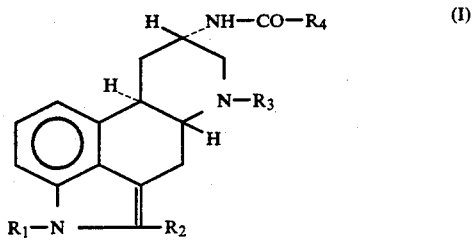

wherein $R_1$ is hydrogen or $C_{1-4}$alkyl, $R_2$ is hydrogen, chlorine, bromine or methyl, $R_3$ is $C_{1-5}$alkyl or $C_{3-5}$alkenyl and $R_4$ is $C_{3-7}$alkyl; $C_{3-7}$cycloalkyl; adamantyl; or optionally substituted phenyl, having valuable pharmaceutical, and in particular LH- and PRL-secretion inhibiting as well as neuroleptic activity.

8 Claims, No Drawings

8α-ACYLAMINOERGOLINES

This is a division of application Ser. No. 07/316,363, filed Feb. 27, 1989 which issued as U.S. Pat. No. 4,950,672 on Aug. 21, 1990, which in turn is a continuation of application Ser. No. 07/167,826, filed Mar. 14, 1988, now abandoned which in turn is a continuation of application Ser. No. 07/011,641, filed Feb. 6, 1987, now abandoned, which in turn is a continuation of application Ser. No. 06/690,864, filed Jan. 11, 1985, now abandoned.

The present invention relates to novel 8α-acylaminoergolines, processes for their production, pharmaceutical compositions containing them and their use as pharmaceuticals.

The 8α-ergolines comprises a major class of compounds possessing varying degrees and type of biological activity and potential therapeutic utility. Thus DOS 25 30 577 and 26 56 344 disclose a wide range of ergoline derivatives which are variously 8α-substituted. Amongst possible 8α-substituents embraced there are included numerous derivatised amino groupings including inter al. acylamino and related residues. The subject compounds are variously described as possessing dopaminergic and prolactin secretion inhibiting activity.

The present invention provides a novel group of 8α-acylamino ergolines, which have been found to possess especially interesting or advantageous biological activity or profile.

More particularly the present invention relates to compounds of formula I

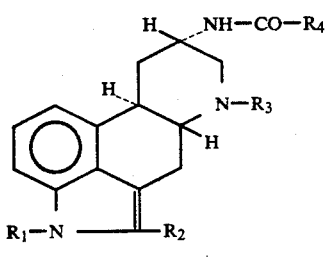

wherein
$R_1$ is hydrogen or $C_{1-4}$alkyl,
$R_2$ is hydrogen, chlorine, bromine or methyl,
$R_3$ is $C_{1-5}$alkyl or $C_{3-5}$alkenyl in which the double bond is not at the carbon atom adjacent to the nitrogen atom, and
$R_4$ is $C_{3-7}$alkyl; $C_{3-7}$cycloalkyl; adamantyl; phenyl; phenyl substituted by one or more members selected from the group consisting of $C_{1-3}$alkyl, $C_{1-3}$alkoxy, $C_{1-3}$alkylthio, trifluoromethyl, hydroxy, nitro, amino and mono- and di-($C_{1-3}$-alkyl)-amino; or phenyl bearing a condensed, non-aromatic, heterocyclic ring having 5- or 6-ring members including 1 or 2 hetero atoms selected from the group consisting of oxygen and sulphur,
with the proviso that when $R_1$ and $R_2$ are both hydrogen and $R_3$ is methyl, $R_4$ is other than t.butyl, as well as the acid addition salts thereof.

A preferred group of compounds of formula I are those of formula Ia

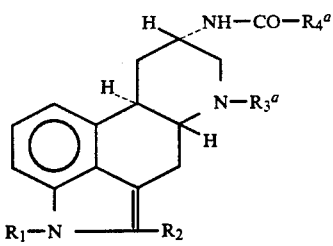

wherein
$R_1$ and $R_2$ have the meanings given for formula I,
$R_3{}^a$ is $C_{2-5}$alkyl or $C_{3-5}$alkenyl in which the double bond is not at the carbon atom adjacent to the nitrogen atom, and
$R_4{}^a$ is (i) $C_{3-7}$alkyl or $C_{3-7}$cycloalkyl; or (ii) phenyl; phenyl substituted by one or two members selected from the group consisting of $C_{1-2}$alkyl, $C_{1-2}$alkoxy, $C_{1-2}$alkylthio, hydroxy and nitro; or phenyl substituted at two adjacent carbon atoms by a divalent residue of formula —O—$CH_2$—O— or —Z—($CH_2$)$_n$—, wherein Z is oxygen or sulphur and n is 2 or 3.

A further preferred group of compounds of formula I are those of formula Ib

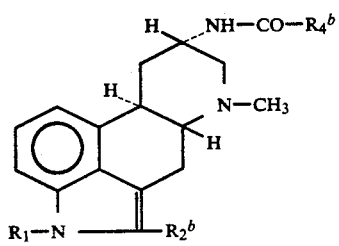

wherein
$R_1$ has the meaning given for formula I,
$R_2{}^b$ is chlorine, bromine or methyl, and
$R_4{}^b$ is $C_{3-7}$alkyl, $C_{3-7}$cycloalkyl or adamantyl.

Alkyl groups and moieties in the compounds of formulae I, Ia or Ib may be straight- or branched-chain.

For the above formula Ia, the following significances, as well as combinations, thereof are preferred:
1. $R_1$ is hydrogen or methyl, especially hydrogen.
2. $R_2$ is hydrogen.
3. $R_3{}^a$ is $C_{3-5}$alkyl, especially n-propyl.
4. $R_4{}^a$ is as previously defined under (ii): $R_4{}^a$ is especially: phenyl; phenyl substituted by one or two members selected from the group consisting of methyl, methoxy, methylthio, hydroxy and nitro; phenyl substituted at two adjacent carbon atoms by the divalent residue of formula —O—$CH_2$—O—; or 2,3-dihydrobenzofuryl-5.

For the above formula Ib, the following significances, as well as combinations thereof, are preferred:
1. $R_1$ is hydrogen or methyl, especially hydrogen.
2. $R_4{}^b$ is $C_{3-7}$alkyl, especially branched-chain $C_{3-7}$alkyl, in particular branched-chain $C_{3-5}$alkyl, most preferably t.butyl.

In one group of compounds of formula I, $R_4$ is $C_{3-7}$alkyl; $C_{3-7}$cycloalkyl; adamantyl; phenyl; phenyl substituted by one or two members selected from the group consisting of $C_{1-3}$alkyl, $C_{1-3}$alkoxy, $C_{1-3}$alkylthio, hydroxy, amino and mono- and di-($C_{1-3}$alkyl)-amino; or phenyl substituted at two adjacent carbon atoms by a divalent residue of formula —O—CH$_2$—O— or —Z—(CH$_2$)$_n$—, wherein Z is oxygen or sulphur and n is 2 or 3.

In one group of compounds of formula Ia, R$_4{}^a$ is (i) C$_{3-7}$alkyl or C$_{3-7}$cycloalkyl; or (ii) phenyl; phenyl substituted by one or two members selected from the group consisting of C$_{1-2}$alkyl, C$_{1-2}$alkoxy, C$_{1-2}$alkylthio and hydroxy; or phenyl substituted at two adjacent carbon atoms by a divalent residue of formula —O—CH$_2$—O— or —Z—(CH$_2$)$_n$— wherein Z is oxygen or sulphur and n is 2 or 3.

The present invention also provides a process for the production of the compounds of formula I and their acid addition salts, which process comprises:

a) reacting a compound of formula II

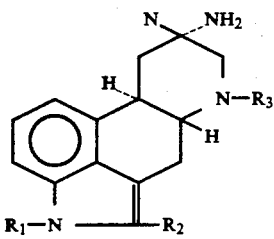

wherein R$_1$, R$_2$ and R$_3$ have the meanings given above with a compound of formula III

R$_4$—COOH            (III)

wherein R$_4$ has the meaning given above, or a reactive functional derivative thereof;

b) Chlorinating or brominating a compound of formula I wherein R$_2$ is hydrogen to produce the corresponding compound of formula I wherein R$_2$ is chlorine or bromine; or c) N-(C$_{1-4}$alkylating) a compound of formula I wherein R$_1$ is hydrogen to produce a corresponding compound of formula I wherein R$_1$ is C$_{1-4}$alkyl; and recovering the obtained compound of formula I as such or as an acid addition salt thereof.

Process step a) may be carried out in accordance with standard procedures. Suitable reactive functional derivatives of the compounds of formula III include e.g. the corresponding acyl halides, in particular chlorides, and imidazolides. Reaction with acylhalides is suitably effected in the presence of a base, such as triethylamine or Hünig-base. Reaction with imidazolides (obtained e.g. by reaction of the compound of formula III with N,N-carbonyldiimidazole) is suitably carried out in an inert solvent such as tetrahydrofuran or ethanol, e.g. at reflux temperature. Where a compound of formula I is employed as such, reaction may suitably be effected e.g. in the presence of propanephosphonic acid anhydride.

Process step b) may also be carried out in accordance with known techniques, using standard chlorinating or brominating agents such as N-Br- or N-Cl-succinimide, sulphuryl chloride or pyrrolidonehydrobromideperbromide. The reaction is conveniently performed in the presence of an inert diluent or solvent such as methylene chloride or tetrahydrofuran.

Process step c) may be carried out in accordance with known methods for the N-alkylation of indolines, e.g. employing a compound of formula IV

R$_1{}^1$-X            (IV)

wherein R$_1{}^1$ is C$_{1-4}$alkyl and X is a leaving group, e.g. a halogen atom, in particular chlorine, fluorine or bromine atom, or methane- or p-toluene-sulfonyloxy group. The reaction is suitably carried out in the presence of an inert solvent or diluent such as dimethylsulfoxide, preferably in the presence of an acid binding agonist such as KOH.

The starting materials of formula II are known or may be produced analogously to the known compounds and in accordance with known procedures. The starting materials for steps b) and c) may be prepared in accordance with process step a).

The compounds of formula I may be recovered from the initially obtained reaction medium as such (i.e. in free base form) or in acid addition salt form e.g. in the form of their pharmaceutically acceptable acid addition salts. Suitable pharmaceutically acceptable acid addition salts include both such salts with inorganic acids, for example the hydrochloride salts, as well as such salts with organic acids, for example the oxalates and maleates.

The following examples are illustrative of the processes for the production of the subject compounds:

EXAMPLE 1

Preparation of 8α-benzoylamino-6-n-propylergoline 1.4 ml benzoylchloride in 5 ml CH$_2$Cl$_2$ are added drop-wise with stirring at 5°–10° C. to a suspension of 3.0 g 8α-amino-6-n-propylergoline in 100 ml CH$_2$Cl$_2$ and 2.0 ml triethylamine. The obtained reaction mixture is stirred for 15 to 20 hours at 20° C. and then washed thoroughly 2× with 25 ml 2N NaOH and H$_2$O. The organic phase is dried over MgSO$_4$, filtered and evaporated. The residue (pale brown foam) is dissolved in ethanol, and crystallised as the hydrobromide by addition of equivalent amounts of HBr in acetic acid. M.P. on recrystallisation from C$_2$H$_5$OH/H$_2$O (80:2)=290° with decomposition.

The following compounds of formula I in which R$_1$=hydrogen are obtained analogously:

| EXAMPLE | R$_2$ | R$_3$ | R$_4$ | M.P. °C. (form) |
|---|---|---|---|---|
| 2 | H | —(CH$_2$)$_2$—CH$_3$ | —C(CH$_3$)$_3$ | 328–330° (Hydrochloride) |
| 3 | H | —(CH$_2$)$_2$—CH$_3$ | Adamantyl-1 | from 265° (Base) |
| 4 | H | —(CH$_2$)$_2$—CH$_3$ | —C(CH$_3$)$_2$—C$_2$H$_5$ | 129° (Base) |
| 5 | H | —CH(CH$_3$)$_2$ | —C(CH$_3$)$_3$ | from 120° (Base) |
| 6 | H | —(CH$_2$)$_2$—CH$_3$ | 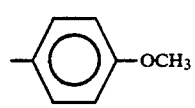 | 208–211° (Mesylate) |

-continued

| EXAMPLE | R$_2$ | R$_3$ | R$_4$ | M.P. °C. (form) |
|---|---|---|---|---|
| 7 | H | —(CH$_2$)$_2$—CH$_3$ | 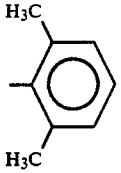 2,6-dimethylphenyl | Base. |
| 8 | H | —(CH$_2$)$_2$—CH$_3$ | 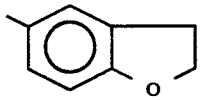 2,3-dihydrobenzofuranyl | Compounds obtained as an amorphous powder - for characterisation see NMR data following. |
| 9 | H | —(CH$_2$)$_2$—CH$_3$ |  2-(methylthio)phenyl |  |
| 10 | H | —(CH$_2$)$_2$—CH$_3$ | 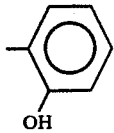 2-hydroxyphenyl |  |
| 11 | H | —(CH$_2$)$_2$—CH$_3$ | 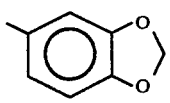 benzo[1,3]dioxolyl | 235–237° (Hydrochloride) |
| 12 | H | —(CH$_2$)$_2$—CH$_3$ | 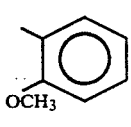 2-methoxyphenyl | 188–190° (Base) |
| 13 | H | —(CH$_2$)$_2$—CH$_3$ | 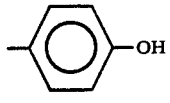 4-hydroxyphenyl | 253–255° (½ Citrate) |
| 14 | H | —(CH$_2$)$_2$—CH$_3$ | 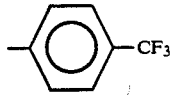 4-(trifluoromethyl)phenyl | 212–214° (½ Fumarate) |
| 15 | H | —(CH$_2$)$_2$—CH$_3$ | 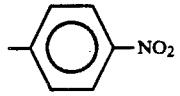 4-nitrophenyl | 230–233° (Hydrochloride) |
| 16 | H | —(CH$_2$)$_2$—CH$_3$ | 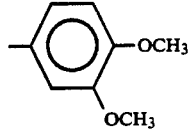 3,4-dimethoxyphenyl | 184–186° (Oxalate) |
| 17 | H | —(CH$_2$)$_2$CH$_3$ | 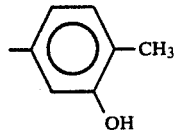 3-methyl-4-hydroxyphenyl | 220–225° (Oxalate) |

-continued

| EXAMPLE | R₂ | R₃ | R₄ | M.P. °C. (form) |
|---------|-----|-----|-----|-----------------|
| 18 | H | —(CH$_2$)$_2$CH$_3$ | 4-OCH$_3$, 3-C$_2$H$_5$-phenyl | from 110° (Base) |
| 19 | CH$_3$ | CH$_3$ | 2-CH$_3$O-phenyl | Base. Amorphous powder. See NMR data following. |
| 20 | CH$_3$ | CH$_3$ | phenyl | 201–202° (Base) |
| 21 | CH$_3$ | CH$_3$ | —C(CH$_3$)$_3$ | 325–330° (Hydrochloride) |
| 22 | CH$_3$ | CH$_3$ | —CH(CH$_3$)$_2$ | 200–204° (Base) |
| 23 | CH$_3$ | CH$_3$ | —C(CH$_3$)$_2$—C$_2$H$_5$ | 210–212° (Base) |
| 24 | CH$_3$ | CH$_3$ | Adamantyl-1 | from 250° (Base) |
| 25 | CH$_3$ | —(CH$_2$)$_2$CH$_3$ | phenyl | Base. Amorphous powder. See NMR data following. |
| 26 | CH$_3$ | —(CH$_2$)$_2$CH$_3$ | —C(CH$_3$)$_3$ | 211–212° (Base) |
| 27 | H | CH$_3$ | Adamantyl-1 | >290° (Base) |
| 28 | H | CH$_3$ | —C(CH$_3$)$_2$—C$_2$H$_5$ | 153° (Base) |
| 29 | H | CH$_3$ | phenyl | 228–230° (Base) |
| 30 | H | CH$_3$ | —CH(CH$_3$)$_2$ | 170–171° (Base) |

The starting material required for the preparation of the compounds of examples 19 to 24, namely 8α-amino-2,6-dimethylergoline, may be prepared as follows:

a) Preparation of 2-Methyl-9,10-Dihydrolysergic Acid Methyl Ester

25 g 2-methyl-lysergic acid in 350 ml H$_2$O and 12.4 ml triethylamine are hydrogenated under normal pressure and at room temperature employing 5% Pd/C. After up-take of the calculated amount of H$_2$, the reaction mixture is filtered over Hyflo concentrated to half volume and adjusted to pH 6 by addition of 1N HCl. The obtained crystalline product is filtered off, dried, taken up in CH$_3$OH/HCl and the obtained suspension stirred at room temperature for 2–3 days until full conversion as determined by thin-layer chromatography. The product is evaporated and subjected to distribution between sodium carbonate and ethyl acetate. After drying and evaporating the title compound is obtained as crystals, which are then rubbed with ethyl ether. M.P.=180°–182° C.

b) Preparation of 2-methyl-9,10-dihydroisolysergic acid methyl ester

43.4 ml of 1.65 molar butyllithium are added at −50° C. under argon to 200 ml tetrahydrofuran and 10.7 ml diisopropylamine. 9.5 g of the product of step a) in 100 ml tetrahydrofuran are added drop-wise after 30 mins. After allowing to stand for 1 hour at −20° C. the pH is adjusted to 7 by the addition of 10% HCl. The mixture is warmed to room temperature, and the organic phase separated and washed 2× with saturated brine. The title compound is obtained after drying and evaporation, filtration of the obtained oil using silica gel and CH$_2$Cl$_2$/MeOH (98:2) as eluant and crystallisation from isopropanol. M.P.=174°–176° C.

c) Preparation of 2-methyl-9,10-dihydrolysergic acid hydrazide

5.95 g hydrazine hydrochloride and 6.8 ml hydrazine hydrate are added to 8.5 g of the product of step b) in 250 ml n-propanol and the obtained reaction mixture heated under reflux. The product is concentrated to half valume, filtered and washed with H$_2$O and filtered by suction to yield the title compound. M.P.=250° C. with decomposition.

d) Preparation of 8α-amino-2,6-dimethyl-ergoline

1.38 g aqueous sodium nitrite are added drop-wise with ice-cooling and stirring to 7.8 g of the product of step c) in 220 ml 0.2N HCl until the pH is ca. 2. When reaction is completed I/Cd paper shows a slight excess of HNO$_2$. The suspension is stirred for a further 30 mins. and added drop-wise to 100 ml 0.4N, refluxing HCl. A clear solution is obtained which is cooled to room temperature, rendered alkaline with 2N soda solution and filtered. The obtained title compound is taken up in C₂H₅OH/ethylacetate (1:1), treated with active charcoal, filtered, concentrated and crystallised from methanol. M.P.=240° C. with decomposition.

The 8α-amino-2-methyl-6-n-propyl-ergoline required as starting material for the production of the compounds of examples 25 and 26, may be obtained in conventional manner from the product of step d) above, via demethylation and n-propylation at the 6-position.

EXAMPLE 31

Preparation of 2-bromo-6-n-propyl-8α-pivaloylamino-ergoline 4.6 g pyrrolindonehydropromideperbromide in 100 ml tetrahydrofuran are added drop-wise to 3.1 g 6-n-propyl-8α-pivaloylaminoergoline (see example 2) in 100 ml tetrahydrofuran pre-cooled to 0° C. After reaction for 2 hours, 1N potassium carbonate is added and the mixture extracted with methylene chloride. The organic phases are dried over Na₂SO₄, concentrated and the residue chromatographed using 100 g silica gel and toluene/ethylacetate (2:1) as eluant. The title compound is obtained on crystallisation from ethylether/hexane. M.P.=182°-183° C.

EXAMPLE 32

Preparation of 2-chloro-6-n-propyl-8α-pivaloylamino-ergoline 1 g silica gel are added to 2 g 6-n-propyl-8α-pivaloylamino-ergoline (example 2) in 50 ml methylene chloride, pre-cooled to 0° C. 0.503 ml sulfurylchloride are added drop-wise and the reaction mixture stirred for 4 hours. 1N potassium carbonate solution is added, the mixture extracted with methylene chloride, dried over Na₂SO₄ and concentrated. The residue is chromatographed on 50 g silica gel using toluene/ethylacetate (2:1) as eluant to yield the title compound. M.P.=146°-147° C.

The following compounds of formula I in which R₁=H may be prepared analogously to the above examples:

| EXAMPLE | R₂ | R₃ | R₄ | M.P. °C. (form) |
|---|---|---|---|---|
| 33 | Br | CH₃ | —C(CH₃)₃ | 211-212° (Base) |
| 34 | Cl | CH₃ | —C(CH₃)₃ | 215-216° (Base) |
| 35 | Cl | CH₃ | —CH₂—C(CH₃)₃ | 192-193° (Base) |
| 36 | Cl | CH₃ | —(CH₂)₂—CH₃ | 116-117° (Base) |
| 37 | Cl | CH₃ | —CH(CH₃)₂ | 141-142° (Base) |
| 38 | Br | —(CH₂)₂—CH₃ | phenyl | 235-237° (Hydrobromide) |
| 39 | Cl | —(CH₂)₂—CH₃ | phenyl | 213-214° (Base) |

EXAMPLE 40

Preparation of 1-methyl-6-n-propyl-8α-(2,3-dihydro-5-benzofuranylamino)-ergoline 696 mg finely powdered KOH and 0.77 ml methyliodide are added to 4.1 g 6-n-propyl-8α-(2,3-dihydro-5-benzofuranylamino)-ergoline (example 9) in 25 ml dimethylsulfoxide. The reactive mixture is stirred for 5 hours, poured onto 150 ml H₂O, extracted with ethyl acetate, dried over Na₂SO₄ and concentrated. The residue is chromatographed on 100 g silica gel using methylene chloride/methanol (98:2) as eluant. M.P.=137°-138° C.

The following compounds of the formula I may be prepared analogously:

| EXAMPLE | R₁ | R₂ | R₃ | R₄ | M.P. °C. (form) |
|---|---|---|---|---|---|
| 41 | —CH(CH₃)₂ | H | —(CH₂)₂CH₃ | phenyl | 136-140° (¼ Fumarate) |
| 42 | —CH(CH₃)₂ | H | —(CH₂)₂CH₃ | 2,3-dihydrobenzofuranyl | 142-143° (Base) |
| 43 | —CH(CH₃)₂ | H | —(CH₂)₂CH₃ | dimethoxyphenyl (OCH₃, OCH₃) | Base. Amorphous powder. See NMR data following. |
| 44 | —CH(CH₃)₂ | H | —(CH₂)₂CH₃ | methylenedioxyphenyl | 158-159° (Base) |
| 45 | —C₂H₅ | H | —(CH₂)₂CH₃ | 2,3-dihydrobenzofuranyl | 112-115° (Base) |

| EXAMPLE | R₁ | R₂ | R₃ | R₄ | M.P. °C. (form) |
|---|---|---|---|---|---|
| 46 | —CH(CH₃)₂ | H | —(CH₂)₂CH₃ | —C(CH₃)₃ | 187–188° (Base) |
| 47 | —CH(CH₃)₂ | H | —(CH₂)₂CH₃ | Adamantyl-1 | 214–215° (Base) |
| 48 | —CH(CH₃)₂ | H | —(CH₂)₂CH₃ | —C(CH₃)₂—C₂H₅ | 192° (Base) |
| 49 | —C₂H₅ | CH₃ | CH₃ | —C(CH₃)₃ | 149–150° (Base) |
| 50 | —CH(CH₃)₂ | H | CH₃ | —C(CH₃)₃ | 162–163° (Base) |
| 51 | CH₃ | H | CH₃ | —C(CH₃)₃ | Base. Amorphors powder - see NMR data following. |
| 52 | —CH(CH₃)₂ | H | CH₃ | 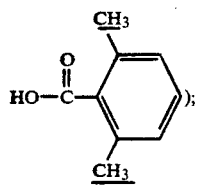 | 191–192 (Base) |

NMR Data—Compounds of Examples 7, 8, 9, 10, 19, 25, 43 and 51:

The following selected, characteristic peaks were observed using NMR spectroscopy, with tetramethyl as reference at 0.0 ppm.

EXAMPLE 7

NMR (CDCl₃, 90 MHz): 0.88 (t, 3H, J=7Hz $\underline{CH_3}$—CH₂—; 2.35 (S, 6H,

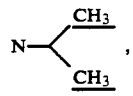

); 4.65 (m, 1H, H—C₈); 6.7–7.3 (m, 9H, arom. H H—C₂, CONH); 8.0 (broad, 1H, N—H).

EXAMPLE 8

NMR (CDCl₃, 90 MHz): 0.91 (t, 3H, J=7 Hz, $\underline{CH_3}$—CH₂—); 4.6 (t, 2H, J=8, —O—$\underline{CH_2}$—); 4.5 (m, 1H, H—C₈); 6.7–7.8 (m, 9H, arom. H, H—C₂, CONH); 8.1 (broad, 1H, N—H).

EXAMPLE 9

NMR (CDCl₃, 360 MHz): 0.9 (t, 3H, J=7 Hz, $\underline{CH_3}$—CH₂—); 2.45 (S, 3H, —S—$\underline{CH_3}$); 4.58 (m, 1H, H—C₈); 6.9–7.6 (m, 9H, arom. H, H—C₂); 7.9 (1H, N—H).

EXAMPLE 10

NMR (CDCl₃, 90 MHz): 0.98 (t, 3H, J=7 Hz, $\underline{CH_3}$—CH₂); 2.5–3.6 (m, 9H, H—C₇, H—C₁₀, H—C₅—H—C₄ₐₓ, H—C₉ₑq, N—CH₂—) 4,55 (m, 1H, H—C₈); 6.7–7.6 (m, 9H, arom. H, CONH, H—C₂); 7.92 (broad, 1H, N—H).

EXAMPLE 19

NMR (CDCl₃, 90 MHz): 2.4 (S, 3H, CH₃—C₂); 2.5 (S, 3H, N—CH₃); 3.92 (S, 3H, O—CH₃); 4.6 (m, 1H, H—C₈); 6.75—7.55 (m, 6H, arom. H) 7.75 (broad, 1H, N—H); 8.1–8.3 (m, 1H, arom. H); 8.8–9.0 (m, 1H, CONH).

EXAMPLE 25

NMR (CDCl₃, 90 MHz): 0.98 (t, 3H, J=7 Hz, $\underline{CH_3}$—CH₂); 2.4 (S, 3H, C₂—CH₃); 4.6 (m, 1H, H—C₈); 6.8–7.9 (m, 10H, arom. H, N—H, CONH).

EXAMPLE 43

NMR (CDCl₃, 360 MHz): 0.97 (t, 3H, J=7 Hz $\underline{CH_3}$—CH₂—); 1.5 (m, 8H, $$N-\begin{matrix}CH_3\\CH_3\end{matrix}$$ , CH₃—CH₂—); 3.91 (S, 3H, O—CH₃); 3.95 (S, 3H, O—$\underline{CH_3}$); 6.8–7.5 (m, 8H, arom. H, CONH).

EXAMPLE 51

NMR (CDCl₃, 90 MHz): 1.2 (S, 9H, t-Butyl); 2.42 (S, 3H, N₆—CH₃); 3.76 (S, 3H, N₁—CH₃); 6.68–7.28 (m, 5H, arom.—H, CONH).

The compounds of formula I and their pharmaceutically acceptable acid addition salts possess pharmacological activity as can be shown in standard animal test methods, and are accordingly useful as pharmaceuticals.

In particular the said compounds and salts possess prolactin (PRL) secretion inhibiting activity as demonstrated e.g. by inhibition of basal prolactin secretion in male rats in the method described by Flückiger et al, Experientia 34, 1330 (1970). Compounds of formula I exhibit activity in this test method at dosages of from 0.0005 to 0.5 mg/kg s.c..

In addition compounds of formula I, in particular compounds of formula Ia, and their pharmaceutically acceptable acid addition salts possess leutenising hormone (LH) secretion inhibiting activity as demonstrated by ovulation inhibition in the following test method [c.f. Marko et al., Life Sciences 33, 233–240 (1983)]:

Female rats (200–250 g) of regular 4 day cycle receive test substance during pro-oestrus at ca. 13.00 and 16.00 hrs. The next morning they are sacrificed, the oviducts examined microscopically and the ova counted. Ovulation is deemed to be inhibited only if no ova are found. The average number of ova counted for each of a series of test animal groups receiving test substance at differing dosages is also recorded in order to permit determination of ED₅₀ values i.e. dosages at which 50% ovulation inhibition is achieved. Compounds of formula Ia exhibit activity in this test method at dosages of from 0.05 to 10.0 mg/kg i.v..

Furthermore compounds of formula I, in particular compounds of formula Ib, and their pharmaceutically acceptable acid addition salts, possess apomorphine antagonistic activity as demonstrated in the test method described by Jansson et al., Arz. Forsch. 10, 1003, (1960). Thus compounds of formula Ib inhibit aporморphine (10 mg/kg s.c.) induced, stereotyped gnawing over periods of several hours, at dosages of from 0.032 mg/kg s.c.

As will be appreciated, activity as PRL secretion inhibitors as demonstrable in the relevant test method described above is also demonstrative of dopamine antagonist acitivity. Furthermore apomorphine antagonist activity as demonstrable (in particular in respect of compounds of formula Ib) in the relevant test method described above is also demonstrable of dopamine antagonist activity. Thus compounds of e.g. formula Ib may be characterised as having a dual dopamine agonist/antagonist activity profile.

In view of their PRL secretion inhibiting activity, compounds of formula I and their pharmaceutically acceptable acid addition salts are useful as PRL secretion inhibitors, e.g. in the treatment of conditions or disorders for which reduction of prolactin levels is indicated, for example for the treatment of galactorrhoea including post-partum galactorrhoea, for the treatment of prolactin-dependent menstrual disorders including amenorrhea, for the inhibition of lactation including post-partum lactation and morbid lactation as well as for the treatment of hyperprolactinaemic hpyogonadism in males and females and of prolactinoma. Furthermore in view of concomitant dopamine agonist activity compounds of formula I and their pharmaceutically acceptable acid addition salts are also useful as dopamine agonists, e.g. for the treatment of Morbus Parkinson.

In view of their LH secretion inhibiting activity compounds of formula I, in particular compounds of formula Ia, and their pharmaceutically acceptable acid addition salts are further useful in the treatment of disorders having an aetiology associated with or modulated by LH secretion or having an aetiology in which the physiological regulation of LH secretion is implicated, for example in the treatment of prostate hypertrophy, in the treatment of menopausal syndrome, in particular post-menopausal hot flashes, as well as the treatment of mammary- and prostatecarcinoma.

In view of their apomorphine antagonistic activity compounds of formula I, in particular compounds of formula Ib, and their pharmaceutically acceptable acid addition salts are useful for use as neuroleptic agents, for example for the treatment of schizophrenia.

It will be further be appreciated that where PRL inhibiting activity is accompanied by apomorphine antagonistic activity, e.g. as in the case of compounds of formula Ib, and the compounds exhibit a dopamine antagonist profile component, the subject compounds and their pharmaceutically acceptable acid addtion salts will be of particular interest for use as PRL secretion inhibitors, having regard to the reduced likelihood of undesirable side-effects (e.g. emetic activity) occurring at endocrinologically active dosages.

For the above uses, the dosage required will of course vary depending on e.g. the particular compound employed, the mode of administrtion, the particular condition to be treated and the effect desired. In general satisfactory results are obtained on administration of compounds of formula I at a daily dosage of:
1) from about 0.0007 to about 0.07 mg/kg body weight for PRL secretion inhibition;
2) from about 0.015 to about 0.15 mg/kg body weight for LH secretion inhibition, and
3) from about 0.015 to about 0.6 mg/kg body weight for apomorphine antagonistic activity.

For the larger mammals an indicated daily dosage is in the range of:
1) from about 0.05 to about 5.0 mg;
2) from about 1 to about 10 mg; and
3) from about 1 to about 40 mg,
of compound of formula I (for use as PRL secretion inhibition; LH secretion inhibition; and apomorphine antagonist utility respectively), conveniently administered in divided doses of 2 to 4×/day in unit dosage form or in sustained release form. Suitable unit dosage forms accordingly comprise:
1) from about 0.01 to about 2.5 mg;
2) from about 0.25 to about 5.0 mg; and
3) from about 0.25 to about 20.0 mg,
(according to intended utility) of compound of formula I together with one or more pharmaceutically acceptable diluents or carriers therefore.

The compounds of the invention may be administered in similar manner to known standards for use in the recited indications.

As previously indicated a suitable daily dosage for any particular compound will depend on a number of factors including its relative potency of activity.

Thus for the compound of example 26, a determined $ID_{50}$ for PRL secretion inhibiting activity in the above cited test method is 0.00056 mg/kg s.c. compared with a measured $ID_{50}$ of 0.007 mg/kg s.c. for the known PRL secretion inhibitor Bromocriptine. Indicated dosages of compound 26 for use in the PRL secretion inhibition indication will accordingly be of the order of ca. 1/10 of those commonly employed using Bromocriptine as drug substance.

For the preferred compound of formula Ia, namely the compound of example 8, a determined $ED_{50}$ in the above described LH inhibition test method is 0.07 mg/kg s.c.

In the above cited test method for determination of apomorphine antagonistic activity, comparison of the preferred compound of formula Ib, namely the compound of example 34 with the known neuroleptic Haloperidol both administered at a dosage of 0.32 mg/kg s.c. indicates that the compound of example 34 exhibits 2× the potency of Haloperidol at 2 hours, with inhibition of stereotyped gnawing lasting for 5 hours in the case of the example 34 compound.

The compounds of formula I may be administered as such or in the form of their pharmaceutically acceptable acid addition salts. Such salts exhibit the same order of activity as the free bases.

The compounds of formula I may be administered by any conventional route, in particular enterally, e.g. orally, for example in the form of tablets or capsules, or parenterally e.g. in the form of injectible solutions or suspensions.

In accordance with the foregoing the present invention also provides.
1) A pharmaceutical composition comprising a compound of formula I as hereinbefore defined or a pharmaceutically acceptable acid addition salt thereof together with a pharmaceutically acceptable diluent or carrier therefor;
2) A compound of formula I as hereinbefore defined or pharmaceutically acceptable acid addition salt thereof for use as a pharmaceutical, i.e. for use in therapy, for example: for use as an PRL secretion inhibitor or for use as a dopamine agonist; or (in particular in the case of compounds of formula Ia as hereinbefore defined and their pharmaceutically acceptable acid addition salts) for use as an LH secretion inhibitor; or (in particular in the case of compounds of formula Ib as hereinbefore defined and their pharmaceutically acceptable acid addition salts) for use as an apomorphine antagonist; and especially for use in any of the specific indications hereinbefore recited in relation to such use; as well as 3) A method of
  3.1.a inhibiting PRL secretion;
  3.1.b treating Morbus Parkinson;
  3.2 inhibiting LH secretion; or
  3.3 effecting neuroleptic treatment, e.g. for treating any of specific conditions hereinbefore recited in relation to such treatment, in a subject in need of such treatment, which method comprises administering to said subject an effective amount of a compound of formula I as hereinbefore defined, and in the case of a method as defined under 3.2, in particular a compound of formula Ia as hereinbefore defined, or in the case of a method as defined under 3.3, in particular a compound of formula Ib as hereinbefore defined, or a pharmaceutically acceptable acid addition salt thereof.

I claim:

1. A method of affecting neuroleptic treatment in a subject in need of such treatment, which comprises administering to said subject a neuroleptic effective amount a compound of the formula I

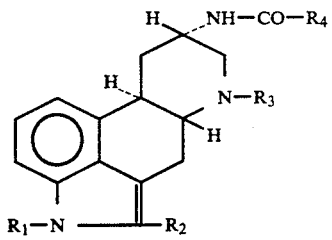

wherein
  $R_1$ is hydrogen,
  $R_2$ is chlorine, bromine or methyl,
  $R_3$ is methyl, and
  $R_4$ is branched chain $C_{3-7}$ alkyl, or an acid addition salt thereof.

2. A method according to claim 1, in which $R_4$ is branched chain $C_{3-5}$ alkyl.

3. A method according to claim 1, in which $R_4$ is t-butyl.

4. A method according to claim 1, in which $R_1$ is hydrogen, $R_2$ is bromine, $R_3$ is methyl and $R_4$ is t-butyl or a pharmaceutically acceptable acid addition salt thereof.

5. A method according to claim 1, in which $R_1$ is hydrogen, $R_2$ and $R_3$ are each methyl and $R_4$ is t-butyl or a pharmaceutically acceptable acid addition salt thereof.

6. A method according to claim 1, in which $R_1$ is hydrogen, $R_2$ is chlorine, $R_3$ is methyl and $R_4$ is t-butyl or a pharmaceutically acceptable acid addition salt thereof.

7. A method according to claim 1, in which from about 1 to 40 mg of the compound of formula I is administered daily.

8. A method according to claim 1, in which from about 0.25 to 20 mg of the compound of formula I is administered in unit dosage form.

* * * * *